United States Patent
Faherty et al.

(10) Patent No.: US 10,046,138 B2
(45) Date of Patent: Aug. 14, 2018

(54) ATRAUMATIC URETERAL ACCESS SHEATH

(71) Applicant: Gyrus ACMI, Inc., Southborough, MA (US)

(72) Inventors: Rich Faherty, Watertown, MA (US); Anthony Tremaglio, Waban, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 843 days.

(21) Appl. No.: 13/961,950

(22) Filed: Aug. 8, 2013

(65) Prior Publication Data
US 2013/0324972 A1 Dec. 5, 2013

Related U.S. Application Data

(63) Continuation of application No. 13/170,060, filed on Jun. 27, 2011, now Pat. No. 8,535,293, which is a (Continued)

(51) Int. Cl.
- *A61M 25/00* (2006.01)
- *A61M 25/06* (2006.01)
- *A61M 25/01* (2006.01)

(52) U.S. Cl.
CPC .... *A61M 25/0053* (2013.01); *A61M 25/0017* (2013.01); *A61M 25/0045* (2013.01); (Continued)

(58) Field of Classification Search
CPC .......... A61M 25/0012; A61M 25/0017; A61M 25/0045; A61M 25/005; A61M 25/0053; A61M 25/0054
See application file for complete search history.

(56) References Cited

U.S. PATENT DOCUMENTS

| | | | | |
|---|---|---|---|---|
| 4,863,442 A | * | 9/1989 | DeMello | A61L 29/041 604/527 |
| 5,554,139 A | * | 9/1996 | Okajima | A61M 25/0053 600/433 |

(Continued)

FOREIGN PATENT DOCUMENTS

| WO | 2001062168 | 8/2001 |
|---|---|---|
| WO | 2005072806 | 8/2005 |

(Continued)

OTHER PUBLICATIONS

Non-final Office Action concerning U.S. Appl. No. 11/105,808, dated Jun. 27, 2006 (7 pages total).

(Continued)

*Primary Examiner* — Laura Bouchelle
(74) *Attorney, Agent, or Firm* — Gerald P. Kazanjian; Pegah Karimi

(57) ABSTRACT

Ureteral access sheaths can have a nonuniform axial-stiffness. A nonuniform axial-stiffness ureteral access sheath can have an inner liner defining a longitudinally extending and generally uniform bore. A non-uniform axial-stiffness outer jacket can define a longitudinally tapered outer surface, and a reinforcement layer can be encapsulated between the inner liner and the non-uniform axial-stiffness outer jacket. The reinforcement layer can have a non-uniform axial-stiffness. For example, a proximal portion of the reinforcement layer can be thicker than a distal portion of the reinforcement layer. A coil of wire can be included in the reinforcement layer, and a diameter of the wire in a proximal portion of the reinforcement layer can be larger than a diameter of the wire in a distal portion of the reinforcement layer. In some instances, the diameter of the wire tapers from the proximal portion to the distal portion.

11 Claims, 9 Drawing Sheets

Related U.S. Application Data continuation-in-part of application No. 11/105,808, filed on Apr. 13, 2005, now Pat. No. 8,235,968.

(60) Provisional application No. 60/561,961, filed on Apr. 13, 2004.

(52) U.S. Cl.
CPC .... *A61M 25/0054* (2013.01); *A61M 25/0662* (2013.01); *A61M 25/0012* (2013.01); *A61M 25/0108* (2013.01); *A61M 2025/0004* (2013.01)

(56) References Cited

U.S. PATENT DOCUMENTS

| | | | | |
|---|---|---|---|---|
| 5,863,366 A * | 1/1999 | Snow | ............... | A61B 17/12022 156/143 |
| 5,938,653 A * | 8/1999 | Pepin | ................ | A61M 25/0009 604/264 |
| 6,217,565 B1 * | 4/2001 | Cohen | ................ | A61M 25/005 604/525 |
| 6,240,231 B1 | 5/2001 | Ferrera et al. | | |
| 6,471,684 B2 | 10/2002 | Dulak et al. | | |
| 6,579,224 B1 | 6/2003 | Burton et al. | | |
| 6,579,277 B1 | 6/2003 | Rabiner et al. | | |
| 6,648,874 B2 * | 11/2003 | Parisi | ................... | A61L 29/085 604/525 |
| 6,702,972 B1 | 3/2004 | Markle | | |
| 7,001,369 B2 | 2/2006 | Griffin et al. | | |
| 7,207,980 B2 | 4/2007 | Christian et al. | | |
| 7,591,783 B2 | 9/2009 | Boulais et al. | | |
| 7,824,392 B2 * | 11/2010 | Zhou | ................... | A61M 25/005 604/523 |
| 8,529,719 B2 | 9/2013 | Pingleton et al. | | |
| 8,535,293 B2 * | 9/2013 | Faherty | ............. | A61M 25/0017 604/525 |
| 2001/0026666 A1 | 10/2001 | Ferrera et al. | | |
| 2004/0193140 A1 * | 9/2004 | Griffin | ............. | A61M 25/0051 604/524 |
| 2008/0033423 A1 | 2/2008 | Peacock | | |

FOREIGN PATENT DOCUMENTS

| | | |
|---|---|---|
| WO | 2007134341 | 11/2007 |
| WO | 2007137184 | 11/2007 |

OTHER PUBLICATIONS

Final Office Action concerning U.S. Appl. No. 11/105,808, dated Dec. 20, 2006 (7 pages total).

* cited by examiner

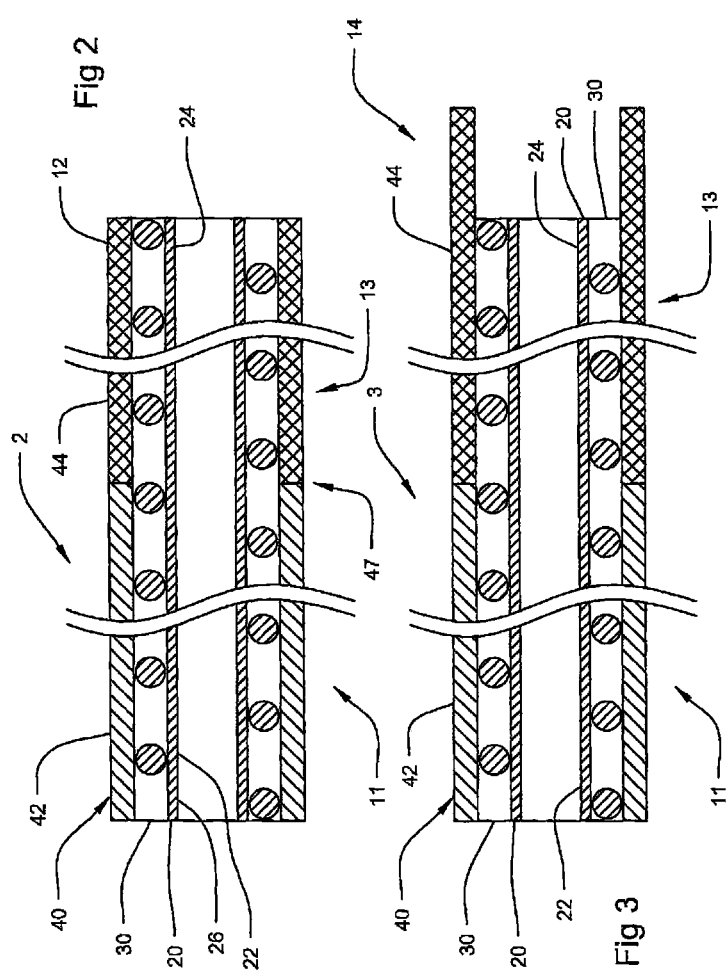

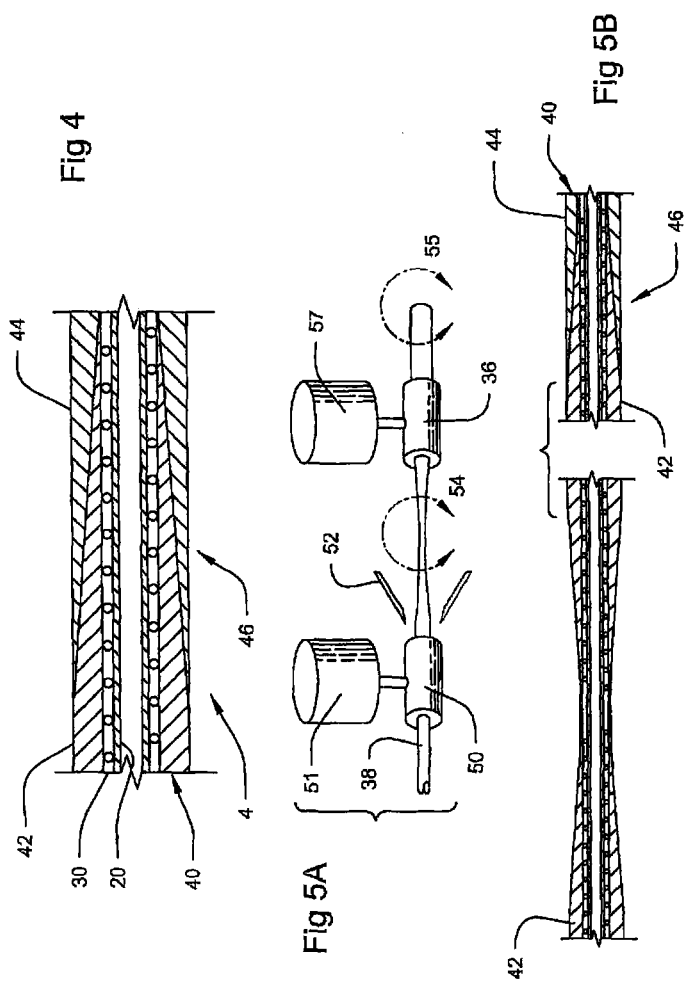

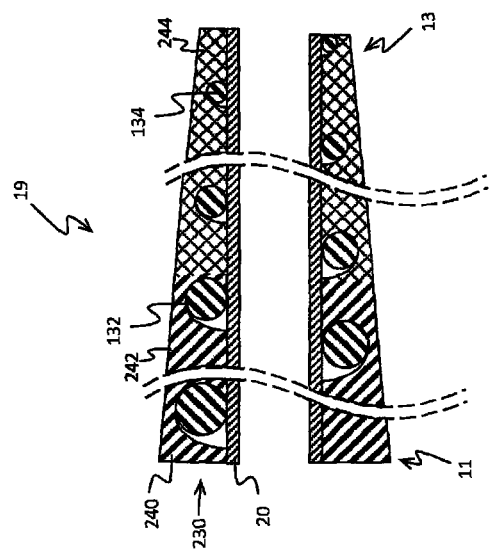
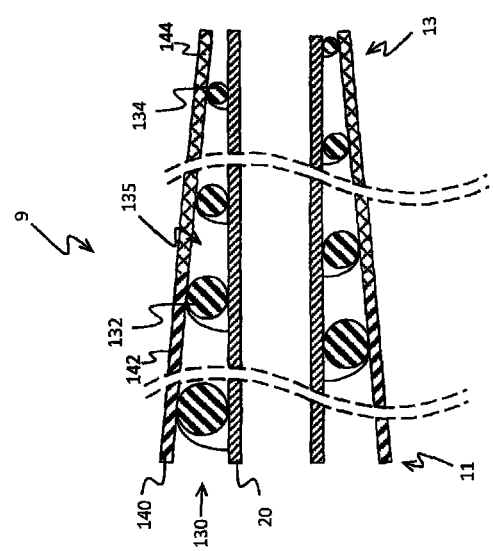

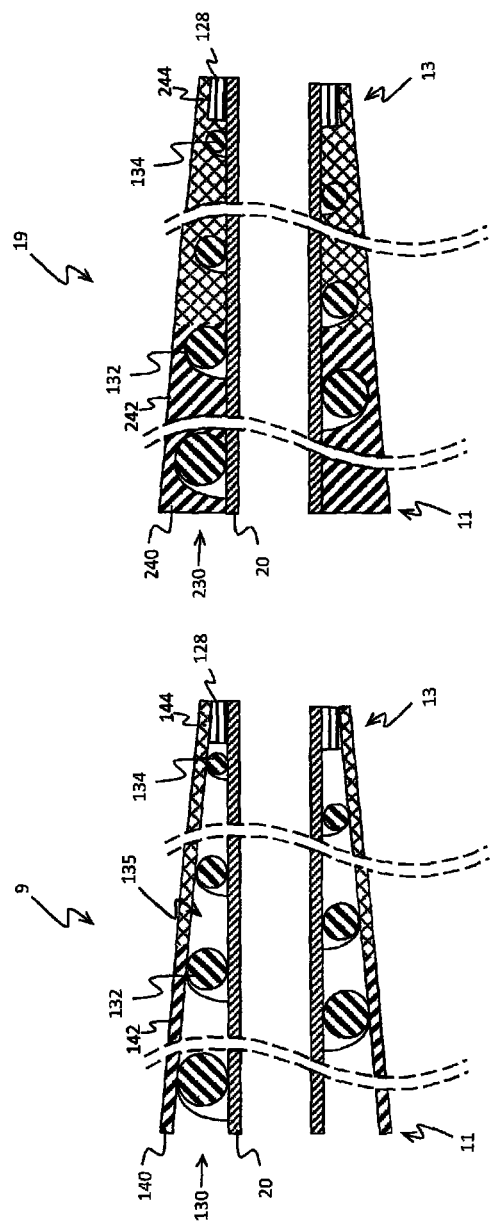

ATRAUMATIC URETERAL ACCESS SHEATH

CROSS-REFERENCE TO RELATED APPLICATIONS

This application is a Continuation-in-Part, claiming the benefit of and priority to U.S. patent application Ser. No. 11/105,808, filed Apr. 13, 2005, which claims the benefit of and priority to U.S. Provisional Application Ser. No. 60/561,961, filed Apr. 13, 2004, the contents of which are both hereby incorporated by reference as if recited in full herein for all purposes.

FIELD

This application, and the innovations and related subject matter disclosed herein, (collectively referred to as the "disclosure") generally relates to access sheaths for insertion into a body cavity or passage, and particularly to ureteral access sheaths.

BACKGROUND

A ureteral access sheath adapted for insertion into a urethra includes an elongate tubular member having a proximal end and a distal end. Known ureteral access sheaths consist of a polytetrafluoroethylene (PTFE) inner liner surrounded by a steel coil reinforcement layer surrounded by a polymer jacket. U.S. Pat. No. 6,471,684 is representative and is hereby incorporated by reference in its entirety. This layered construction results in the axial-stiffness of the sheath being substantially uniform along its entire length, including the distal tip. While proximal axial-stiffness is desirable for pushability during placement, the resultant distal axial-stiffness can cause trauma to the ureter. Further, the tip construction of known sheaths consists of a stiff polymer material that has little ability to cushion the impact upon tissue that it contacts.

SUMMARY

Some embodiments of disclosed innovations provide a nonuniform axial-stiffness ureteral access sheath comprising a nonuniform axial-stiffness jacket and an inner liner encapsulating a reinforcement layer there between. Other embodiments provide a nonuniform axial-stiffness ureteral access sheath comprising a nonuniform axial-stiffness reinforcement layer encapsulated between a uniform axial-stiffness jacket and an inner liner. Other embodiments provide a nonuniform axial-stiffness ureteral access sheath comprising a nonuniform axial-stiffness jacket and inner liner encapsulating a nonuniform axial-stiffness reinforcement layer.

Embodiments of the nonuniform axial-stiffness ureteral access sheath provide a ureteral access sheath that is more pushable at the relatively more-stiff proximal end and less traumatic to the tissue, as well as more trackable, at the relatively less-stiff distal end, with the capability to provide a wide range of predictable variations in axial-stiffness and other structural parameters over the length of the nonuniform axial-stiffness ureteral access sheath.

The foregoing and other features and advantages will become more apparent from the following detailed description, which proceeds with reference to the accompanying drawings.

BRIEF DESCRIPTION OF THE DRAWINGS

The accompanying drawings show aspects of the innovative sheaths disclosed herein, unless specifically identified as showing a known feature from the prior art.

FIG. 2 is a side cross-sectional view of a nonuniform axial-stiffness ureteral access sheath;

FIG. 3 is a side cross-sectional view of another nonuniform axial-stiffness ureteral access sheath;

FIG. 4 is a side cross-sectional view of another nonuniform axial-stiffness ureteral access sheath;

FIG. 5A is a schematic of a process for making a nonuniform axial-stiffness ureteral access sheath;

FIG. 5B is a side cross-sectional view of a nonuniform axial-stiffness ureteral access sheath at various stages of fabrication;

FIG. 10 is a side cross-sectional view of another nonuniform axial-stiffness ureteral access sheath;

FIG. 11 is a side cross-sectional view of another nonuniform axial-stiffness ureteral access sheath;

FIG. 12 is a side cross-sectional view of another nonuniform axial-stiffness ureteral access sheath; and FIG. 13 is a side cross-sectional view of another nonuniform axial-stiffness ureteral access sheath.

DESCRIPTION

In the following detailed description, reference is made to the accompanying drawings which form a part hereof wherein like numerals designate like parts throughout, and in which is shown by way of illustration specific embodiments in which the invention may be practiced. It is to be understood that other embodiments may be utilized and structural or logical changes may be made without departing from the scope of the present invention. Therefore, the following detailed description is not to be taken in a limiting sense, and the scope of the present invention is defined by the appended claims and their equivalents.

Some innovative embodiments provide a nonuniform axial-stiffness ureteral access sheath comprising a nonuniform axial-stiffness outer jacket and an inner liner encapsulating the reinforcement layer there between. Other innovative embodiments provide a nonuniform axial-stiffness ureteral access sheath comprising a nonuniform axial-stiffness reinforcement layer encapsulated between a single axial-stiffness outer jacket and the inner liner. Other innovative embodiments provide a nonuniform axial-stiffness ureteral access sheath comprising a nonuniform axial-stiffness outer jacket and an inner liner encapsulating the reinforcement layer there between.

Embodiments of the nonuniform axial-stiffness ureteral access sheath provide a ureteral access sheath that is more pushable at the relatively more-stiff proximal end and less traumatic to the tissue, as well as more trackable, at the relatively less-stiff distal end, with the capability to provide a wide range of predictable variations in axial-stiffness and other structural parameters over the length of the nonuniform axial-stiffness ureteral access sheath.

Figure 1:
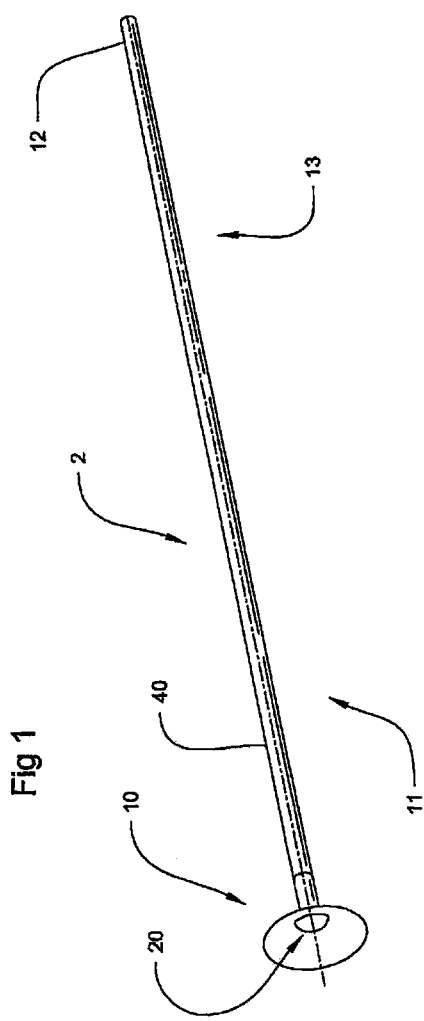
FIG. 1 is a side perspective view of a nonuniform axial-stiffness ureteral access sheath.

FIG. 1 is a side perspective view of a nonuniform axial-stiffness ureteral access sheath 2. The embodiment accordingly provides a nonuniform axial-stiffness ureteral access sheath 2 for placement within the ureter system. The nonuniform axial-stiffness ureteral access sheath 2 comprises an elongated tubular member having a sheath proximal end 10 and a sheath distal end 12. The elongated tubular member comprises a tubular inner liner 20, a coaxial reinforcement layer 30, and a coaxial outer jacket 40.

FIG. 2 is a side cross-sectional view of a nonuniform axial-stiffness ureteral access sheath 2 comprising an outer jacket 40 comprising a first jacket portion 42 having a material composition that is more stiff (a higher durometer) at the sheath proximal portion 11 and a second jacket portion 44 having a material composition that is less stiff (a lower durometer) at the sheath distal portion 13. As used herein, "composition" of a material means, for example, a chemical composition of the material, as well as a construction, form, phase and/or structure of the material.

The inner liner 20 extends essentially the entire length of the ureteral access sheath 2, from a liner proximal end 22 to a liner distal end 24. The reinforcement layer 30 extends coaxially over the inner liner 20 from the liner proximal end 22 to the liner distal end 24. The outer jacket 40 extends coaxially over the reinforcement layer 30 from the liner proximal end 22 to the liner distal end 24.

The inner layer 20 comprises a material suitable for a particular purpose. The ureteral access sheath 2 is used to provide a passageway through which instruments are passed. Therefore, the inner liner 20 must withstand the impact and abrasion that might be caused the passing instruments. Material suitable for comprising the inner liner 20 include, but not limited to, polytetrafluoroethylene (PTFE), polyethylene terephthalate (PET), polyether ethyl ketone (PEEK), polyphenylene sulfide (PPS), or any of a variety of other polymers suitable for the particular purpose.

The reinforcement layer 30 comprises a material suitable for a particular purpose, such as for providing a desired predetermined axial-stiffness, such as to resist buckling, along the length of the ureteral access sheath 2. Material suitable for the reinforcement layer 30 includes, but is not limited to fibers comprising a polymer, metal, or both.

Embodiments of the reinforcement layer 30, include, but are not limited to, a braid, mesh or coil. The reinforcement layer 30 can consist of longitudinal, angled or circumferential windings of high strength fibers which are bonded to the inner liner 20 and covered by the outer jacket 40. Embodiments of the reinforcement layer 30 further comprises a matrix of material between the fibers, such as, but not limited to the outer jacket 40 conforming to the spaces between the fibers, braid, mesh or coil, among others.

In an embodiment, the reinforcement layer 30 is a coil, such as a round or flat wire coil. The coil is coaxially placed over the inner liner 20 and the assembly is encapsulated within an outer jacket 40 providing a smooth, low friction outer surface. In another embodiment, the reinforcement layer 30 is a tubular mesh braid, such as, but not limited to, stainless steel and composite. Those skilled in the art will recognize that the orientation and composition of the reinforcing fibers along and about the inner liner 20 can be altered over a wide range to provide a predetermined axial-stiffness. The reinforcement layer 30 is attached over the inner liner and adhesively or mechanically bonded to the inner liner 20.

In another embodiment, the nonuniform axial-stiffness ureteral access sheath 2 comprises an outer jacket 40 comprising at least two tandemly disposed coaxial tube portions, including a proximal jacket portion 42 and a distal jacket portion 44, the tube portions having dissimilar axial-stiffness, with the stiffest being located at the sheath proximal portion 11 and the least stiff located at the sheath distal portion 13 of the ureteral access sheath 2. This construction provides the ureteral access sheath with a minimum of two regions of different axial-stiffness and flexibility.

The outer jacket 40 comprises a material suitable for a particular purpose. The material provides a smooth and low friction outer surface while encapsulating the reinforcement layer 30 in cooperation with the inner liner 20. Any of a variety of polymeric material is suitable for the particular purpose for providing a desired predetermined axial-stiffness to thereby provide desired axial-stiffness along the length of the ureteral access sheath 2. The durometer of the polymer of the sheath proximal portion 11 is substantially higher than the durometer of the polymer of the sheath distal portion 13. This allows the ureteral access sheath 2 to have the proximal pushability needed for placement and distal flexibility to minimize trauma to the ureter. In other embodiments to be explained below, the sheath distal portion 13 includes an end formed of the softer polymer that cushions the impact or irritation to tissue.

The jacket proximate portion 42 can be made of a higher durometer elastomeric and the jacket distal portion 44 is made of a lower durometer polymer. Various material compositions can provide the desired durometer properties, such as, but not limited to Nylon, Urethane, and Hytrel, which are known in the art.

Those skilled in the art will recognize that a variety of polymers, including those filled with reinforcing fibers or other material may be used to reinforce the outer jacket 40 in order to provide a structure with specific and desired combinations of axial-stiffness, torqueability, and pushability over the length of the ureteral access sheath 2. For example, the characteristics of the materials to be used may be optimized by use of joining adjacent portions of different materials against one another longitudinally in end to end fashion in a butt transition 47 to thus provide a constant outer diameter. In such a construction, the outer jacket 40 is formed of joined, such as by heat and/or pressure, or adhering bonded sections surrounding specific portions of the assembly of the inner liner 20 and reinforcement layer 30. Similarly, such a construction can be combined with an outer jacket 40 to provide a smooth overall exterior to the finished nonuniform axial-stiffness ureteral access sheath 2.

A variety of techniques can be used to achieve the nonuniform axial-stiffness of the outer jacket 40. Such techniques include, but are not limited to, the butt welding of tubular segments of material with a different axial-stiffness from one another to form the outer jacket 40, and use of an adhesive to bond the outer jacket 40 to the assembly comprising the inner liner 20 and the reinforcement layer 30. In other embodiments of methods of fabricating the ureteral access sheath 2, heat is applied to the coaxial layers, resulting in consolidation to encapsulate the reinforcement layer 30 between the inner liner 20 and the outer jacket 40.

The embodiment of the nonuniform axial-stiffness ureteral access sheath 2 shown in FIG. 1 further comprises a proximal end 10 that is flared to accept and guide medical instruments therein and through the lumen 20, shown by way of example. It is understood that the proximal end 10 may not be flared, as is common in the art. It is also understood that the proximal end 10 may be adapted to couple with a flared portion so as to provide a flared proximal end 10 having the same inner diameter as the rest of the proximal portion 11.

FIG. 3 is a side cross-sectional view of a nonuniform axial-stiffness ureteral access sheath 3 comprising an outer jacket 40 having a jacket proximal portion 42 comprising a first composition that is more stiff at the sheath proximal portion 11 and a jacket distal portion 44 comprising a second composition that is less stiff at the sheath distal portion 13, wherein the outer jacket 40 extends beyond the inner liner 20 and reinforcement layer 30 to define a distal tip 14.

The inner liner 20 extends essentially the entire length of the ureteral access sheath 3, from a liner proximal end 22 to a liner distal end 24. The reinforcement layer 30 extends coaxially over the inner liner 20 from the liner proximal end 22 to the liner distal end 24. The outer jacket 40 extends over the reinforcement layer 30 from the liner proximal end 22 to a predetermined distance beyond the liner distal end 24 defining an extended tip portion 14 that is not co-layered with the reinforcement layer 30 and the inner liner 20; the outer jacket 40 defining essentially the entire length of the ureteral access sheath 3.

FIG. 4 is a side cross-sectional view of an innovative nonuniform axial-stiffness ureteral access sheath 4 comprising an outer jacket 40 having a jacket proximal portion 42 comprising a first composition that is more stiff at the sheath proximal portion 11 and a jacket distal portion 44 comprising a second composition, comprising a tapered transition portion 46 between the less-stiff portion and the more-stiff portion.

FIG. 5A is a schematic of an innovative process for making a nonuniform axial-stiffness ureteral access sheath 4 comprising an outer jacket 40 having a jacket proximal portion 42 comprising a first composition that is more stiff at the sheath proximal portion 11 and a jacket distal portion 44 comprising a second composition that is less stiff at the sheath distal portion 13, comprising a tapered transition between the less-stiff portion and the more-stiff portion. Two different polymers are deposited at complimentary rates in successive dies to provide a double tapered jacket of consistent outside diameter.

In the process of FIG. 5A, an assembly 38 comprising the inner liner 10 and reinforcement layer 30 is passed at a controlled speed by a feeding mechanism (not shown) through a first die 50 receiving a polymer material from a supply 51 to be deposited on the assembly 38 at a rate controlled by the speed of the assembly 38 through the first die 50. The size of the first die 50 and the temperature and composition of the polymer and the speed can be varied to deposit a thicker or thinner layer and to taper the deposit as shown at 54. If desired, quenching jets 52 can be used to cool the polymer after deposit. One or more additional dies 56 applies a second polymer from supply 57 to create an additional layer of polymer of a different characteristic from the first and to form a consistent diameter as shown at 55.

In practice, this construction allows for control of both the outer diameter of the finished ureteral access sheath and wide variations in the axial-stiffness of the ureteral access sheath over its length, depending on the material being deposited and the relative thickness of the softer and harder layers.

FIG. 5B is a side cross-sectional view of a nonuniform axial-stiffness ureteral access sheath comprising an outer jacket 40 having a jacket proximal portion 42 comprising a first composition that is more stiff at the sheath proximal portion 11 and a jacket distal portion 44 comprising a second composition that is less stiff at the sheath distal portion 13, and comprising a tapered transition 46 between the less-stiff portion and the more-stiff portion, at various stages of fabrication. FIG. 5B illustrates a cross section of the ureteral access sheath 4 according to this embodiment, showing the increased tapering of softer and harder portions of the deposited outer jacket 40 to provide a desired nonuniform axial-stiffness ureteral access sheath 40 during the course of manufacture.

Those skilled in the art will recognize that a variety of the above described embodiments can be combined to provide a wide range of desired characteristics to the finished composite ureteral access sheath.

Figure 6:
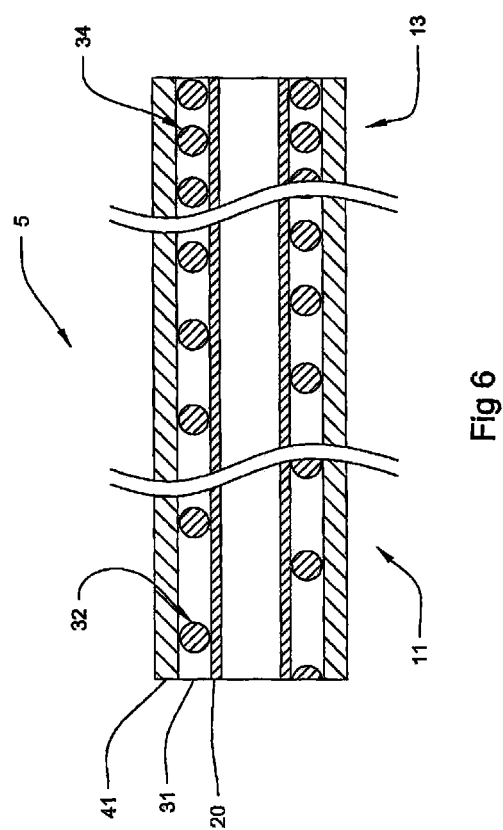
FIG. 6 is a side cross-sectional view of another nonuniform axial-stiffness ureteral access sheath.

FIG. 6 is a side cross-sectional view of a nonuniform axial-stiffness ureteral access sheath 5 comprising a reinforcement layer 31 that is stiffer at a reinforcement layer proximal portion 32 and less stiff at a reinforcement layer distal portion 34. By using such innovative construction techniques, a reinforcement layer 31, such as, but not limited to, a braid or coil, of a predetermined non-uniformity of longitudinal axial-stiffness encapsulated between the inner liner 20 and a uniform axial stiffness outer jacket 41, provides a lower axial-stiffness at the sheath distal portion 13 providing a softer, better tracking device, and a higher axial-stiffness at the sheath proximal end 11 to provide improved pushability.

The reinforcement layer 31 has a composition such as a polymer, metal, or both, for providing a predetermined multiple longitudinal axial-stiffness to thereby provide desired variations in axial-stiffness along the length of the ureteral access sheath 5.

In yet other innovative embodiments, the reinforcement layer 31 comprises longitudinal, angled or circumferential windings of high strength fibers which are bonded to the inner liner 20 and covered by the outer jacket 41. By use of such a construction, wide variations in axial-stiffness and other physical parameters are obtained.

As is illustrated in FIG. 6, an embodiment of a reinforcement layer 31 is a coil, such as a round or flat wire coil, applied over the inner liner 20. Those skilled in the art will recognize that the orientation and composition of the reinforcing strands along and about the ureteral access sheath 5 can be altered over a wide range to provide any number of desirable characteristics related to flexibility and axial-stiffness.

The proximal and distal axial-stiffness of the reinforcement layer 31 can also be further modified by the type of reinforcement wire used, the size of the wire used (e.g., FIGS. 10 and 11), the pitch between the coils of the wire or between the strands of the braid and the number of strands of wire that are used.

In some innovative embodiments, the reinforcement layer 31 comprises a tubular metal wire braid, such as, but not limited to stainless steel, is adhesively or mechanically bonded to the inner liner 20. The reinforcement layer 31 can alternatively be formed of a reinforcing composite material, such as, but not limited to, glass fiber.

Figure 7:
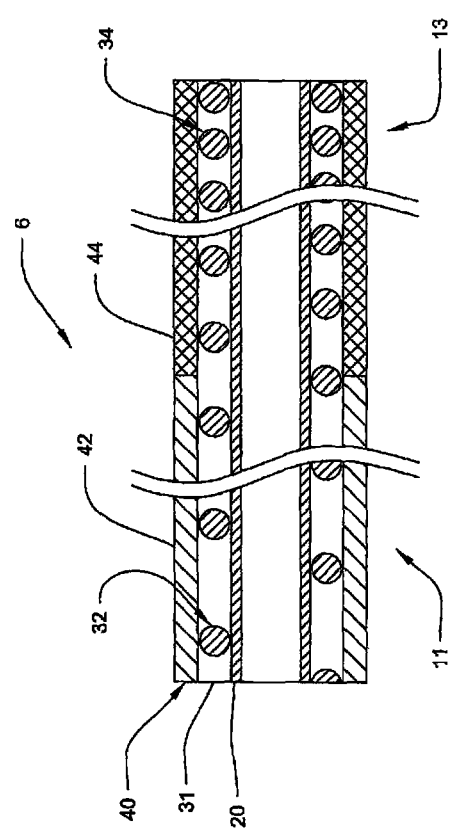
FIG. 7 is a side cross-sectional view of another nonuniform axial-stiffness ureteral access sheath.

FIG. 7 is a side cross-sectional view of an innovative nonuniform axial-stiffness ureteral access sheath 6 comprising a nonuniform axial stiffness outer jacket 40 and a nonuniform axial stiffness reinforcement layer 31 that is more stiff at the sheath proximal end 11 and less stiff at the sheath distal end 13. The combination of a nonuniform axial stiffness outer jacket 40 and nonuniform axial stiffness reinforcement layer 31 provides predetermined nonuniform axial stiffness to the ureteral access sheath 6 suitable for a particular purpose.

Figure 8:
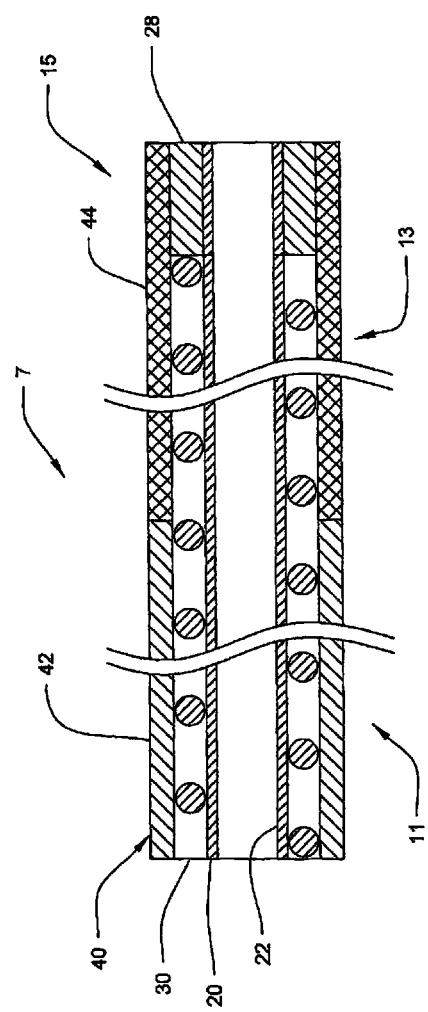
FIG. 8 is a side cross-sectional view of another nonuniform axial-stiffness ureteral access sheath.

FIG. 8 is a side cross-sectional view of an innovative nonuniform axial-stiffness ureteral access sheath 7. The nonuniform axial-stiffness ureteral access sheath comprises an outer jacket 40 having a jacket proximal portion 42 comprising a first composition that is more stiff at the sheath proximal portion 11 and a outer jacket distal portion 44 comprising a second composition that is less stiff at the sheath distal portion, wherein the outer jacket 40 and the inner liner 20 extend beyond the reinforcement layer 30 to define a distal tip 15. The extension of the outer jacket 40 and the inner liner 20 defines a space there between, wherein a radiopaque element 28 is disposed. In the embodiment of FIG. 8, the radiopaque element 28 is in the form of a band.

Radiopaque markers are commonly used in medical devices so that the device can be located within the body using radiological imaging. For example, having the radiopaque element 28 in the distal tip 15 as provided in the embodiment of FIG. 8, the distal tip 15 can be visualized during insertion into the ureter for proper placement.

In another innovative embodiment, a method of constructing the nonuniform stiffness ureteral access sheath comprises: providing an elongated tubular inner liner, the elongated tubular inner liner having a liner proximal end and a liner distal end; coaxially placing a tubular reinforcement layer over the inner liner extending from the liner proximal end and spaced a predetermined distance from the liner distal end; coaxially placing a tubular radiopaque element on the inner liner extending from the reinforcement layer to the liner distal end; and applying at least one layer of material over the reinforcement layer and the radiopaque element.

In other innovative embodiments, a radiopaque element comprises the reinforcement layer 30 itself, the reinforcement layer 30 comprising a radiopaque material. Radiopaque material is known in the art, including, but not limited to, platinum, gold and tungsten.

Figure 9:
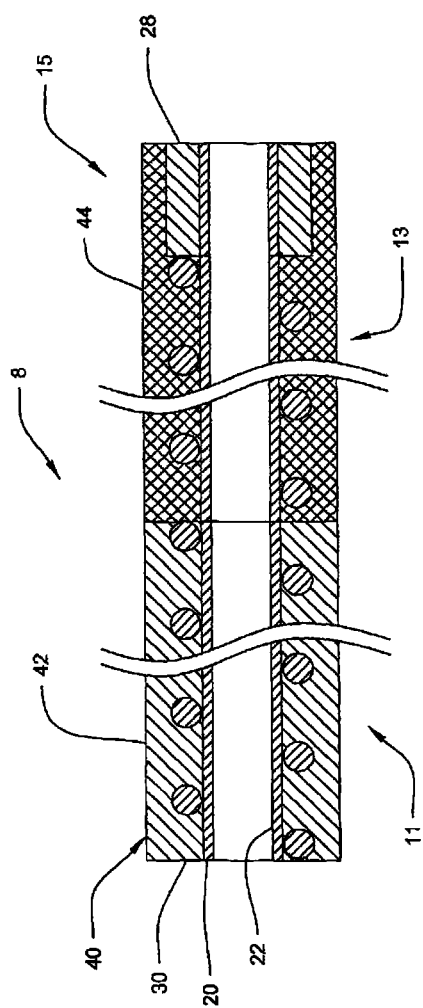
FIG. 9 is a side cross-sectional view of another nonuniform axial-stiffness ureteral access sheath.

FIG. 9 is a side cross-sectional view of an innovative nonuniform axial-stiffness ureteral access sheath 8. The nonuniform axial-stiffness ureteral access sheath comprises an outer jacket 40 having a jacket proximal portion 42 comprising a first composition that is more stiff at the sheath proximal portion 11 and a outer jacket distal portion 44 comprising a second composition that is less stiff at the sheath distal portion, wherein the outer jacket 40 and the inner liner 20 extend beyond the reinforcement layer 30 to define a distal tip 15. As illustrated in FIG. 9, the jacket proximal portion 42 and the jacket distal portion 44 are respectively in contact with a radial outer surface of the inner liner 20. The extension of the outer jacket 40 and the inner liner 20 defines a space there between, wherein a radiopaque element 28 is disposed. In the embodiment of FIG. 9, the radiopaque element 28 is in the form of a band.

FIG. 9 illustrates how the outer jacket 40 can conform to the profile of the elements of the reinforcement layer 30, encasing the reinforcement layer 30 in cooperative arrangement with the inner liner 20. It is understood that the cooperative arrangement between the outer jacket 40 and the inner liner 20 as shown in FIG. 9 is also applicable to any of the above embodiments previously presented. Material properties of the material used for outer jacket 40 can be predetermined so as to deform, flow, conform to, and otherwise encapsulate the fibers of the reinforcement layer 30 during the manufacturing process.

Embodiments of the reinforcement layer 30, include, but are not limited to, a braid, mesh or coil. The reinforcement layer 30 can consist of longitudinal, angled or circumferential windings of high strength fibers which are bonded to the inner liner 20 and encased by the outer jacket 40. The outer jacket 40 conforms to the spaces between the fibers, braid, mesh or coil, among others.

FIG. 10 is a side cross-sectional view of a nonuniform axial-stiffness ureteral access sheath 9 comprising an outer jacket 140. The jacket 140 comprises a first jacket portion 142 that is relatively stiffer than a second jacket portion 144. The first jacket portion 142 and the second jacket portion 144 are coaxially and tandemly disposed over structures of a reinforcement layer 130. In the illustrated embodiment, the first jacket portion has a material composition that is relatively more stiff (e.g., has a higher durometer) at the sheath proximal portion 11 than the material composition at the second jacket portion 144 adjacent the sheath distal portion 13.

As with other disclosed embodiments, the inner liner 20 can extend essentially the entire length of the ureteral access sheath 9. As with the embodiment shown in FIG. 3, the liner 20 can extend less than the entire length of the sheath 9. The inner liner 20 can have any suitable composition, as described above.

The reinforcement layer 130 extends coaxially over the inner liner 20 and tapers from a larger dimension adjacent the proximal end 11 to a smaller dimension adjacent the distal end 13. The outer jacket 140 extends coaxially over the tapered reinforcement layer 130 from the proximal end 11 to the distal end 13, encapsulating the reinforcement layer between the outer jacket 130 and the inner liner 20. A material composition of the outer jacket 140 can be selected from the compositions described above in connection with any other disclosed embodiments of nonuniform axial-stiffness sheaths.

The reinforcement layer 130 comprises a material suitable for a particular purpose, such as for providing a desired predetermined axial-stiffness, such as to resist buckling, along the length of the ureteral access sheath 2. Material suitable for the reinforcement layer 30 includes, but is not limited to fibers comprising a polymer, metal, or both.

Embodiments of the tapered reinforcement layer 130, include, but are not limited to, a braid, mesh or coil. The reinforcement layer 130 can comprise longitudinal, angled or circumferential windings of high strength fibers which are bonded to the inner liner 20 and covered by the outer jacket 140. Embodiments of the reinforcement layer 130 can further comprise a matrix of material between the fibers, such as, but not limited to the outer jacket 140 conforming to the spaces between the fibers, braid, mesh or coil, among others.

As noted above in connection with the sheath 5 shown in FIG. 6, the orientation and composition of the reinforcing strands of the reinforcement layer 130 positioned along and about the ureteral access sheath 9 can be altered over a wide range to provide any number of desirable characteristics related to flexibility and axial-stiffness. The proximal and distal axial-stiffness of the reinforcement layer 130 can also be further modified by the type of reinforcement wire used, the size of the wire used, the pitch between the coils of the wire or between the strands of the braid and the number of strands of wire that are used.

For example, as shown in FIG. 10, the reinforcement layer 130 can comprise a tapered coil, such as, for example, a tapered round or tapered flat wire having a larger proximal portion 132 and a smaller distal portion 134 and being helically wound (as around a mandrel) to form the tapered coil. The tapered coil is coaxially placed over the inner liner 20 and the assembly is encapsulated within the outer jacket 140 providing a smooth, low friction outer surface. In another embodiment, the reinforcement layer 130 is a tapered, tubular mesh braid, such as, but not limited to, stainless steel and composite. Those skilled in the art will recognize that the orientation, taper and composition of reinforcing fibers along and about the inner liner 20 can be altered over a wide range to provide the reinforcement layer 130 with a predetermined axial-stiffness. The reinforcement layer 130 can be attached over the inner liner 20 and adhesively or mechanically bonded to the inner liner.

The nonuniform axial-stiffness outer jacket 140 can taper longitudinally, as shown in, for example, FIGS. 4 and 10. As indicated in FIG. 4, a thickness of the proximal jacket portion 42 or the distal jacket portion 42 of the outer jacket 40 can taper longitudinally, while a diameter of the outer jacket 40 can remain substantially uniform longitudinally. As indicated in FIG. 10, a thickness of the outer jacket 140 can remain substantially uniform longitudinally, while a diameter of the outer jacket can taper. In either instance, the nonuniform axial-stiffness outer jacket 140 can define a tapered outer surface having a larger dimension adjacent the proximal end 11 to a smaller dimension adjacent the distal end 13, as shown for example in FIG. 10.

Although the illustrated jacket 140 has a first material composition in the first jacket portion 142 and a second material composition in the second jacket portion 144, the jacket 140 can have a substantially homogeneous material composition from the first jacket portion 142 to the second jacket portion 144. Even with a substantially homogeneous material composition, a longitudinally tapered outer jacket 140 having a larger outer dimension adjacent a proximal portion 11 and a smaller outer dimension adjacent a distal portion 13, as shown in FIG. 10, can provide a relatively higher proximal stiffness compared to a distal stiffness.

As shown, for example, in FIG. 10, there can be a space 135 between the inner liner 20 and a length of the nonuniform axial-stiffness outer jacket 140 spanning the jacket distal portion 144 and the jacket proximal portion 142 that are devoid of reinforcement layer structure. In some embodiments, such as, for example, shown in FIG. 10, a portion of the inner liner can be so spaced from the outer jacket as to define a region devoid of reinforcement layer structure. The space 135 between the inner liner 20 and the outer jacket 140 can be positioned between structures of the reinforcement layer 130, as shown in, for example, FIGS. 2 and 10. In other instances, a space between the inner liner 20 and the outer jacket 140 devoid of reinforcement layer structure can be positioned adjacent an end of the sheath, as shown in FIG. 12. In FIG. 12, the space devoid of reinforcement layer structure, positioned adjacent an end of the sheath, is at least partially occupied by the radiopaque element 128.

FIG. 11 illustrates another embodiment of a tapered nonuniform axial-stiffness sheath 19 encapsulating the reinforcement layer 130. As with the sheath 8 shown in FIG. 9, the outer jacket 240 can conform to the profile of the elements of the reinforcement layer 230, encasing the reinforcement layer 230 in cooperative arrangement with the inner liner 20. It is understood that the cooperative arrangement between the outer jacket 240 and the inner liner 20 as shown in FIG. 11 is also applicable to any of the above embodiments previously presented. Material properties of the material used for outer jacket 240 can be predetermined so as to deform, flow, conform to, and otherwise encase the fibers of the reinforcement layer 230 during the manufacturing process.

Embodiments of the tapered reinforcement layer 230, include, but are not limited to, a braid, mesh or coil. As with the tapered reinforcement layer 130 described in connection with FIG. 10, the reinforcement layer 230 can have longitudinal, angled or circumferential windings of high strength fibers which are bonded to the inner liner 20 and encased by the outer jacket 240.

In the embodiment shown in FIG. 11, the tapered outer jacket 240 conforms to a space between the inner liner 20 and the nonuniform axial-stiffness outer jacket 240. As with the jacket shown in FIG. 9, a portion of the inner liner 20 can be so spaced from the outer jacket 240 as to define a region occupied by the structure of the reinforcement layer 230 or by the radiopaque element 228. A space between the inner liner 40 and the outer jacket 240 devoid of reinforcement layer structure can be positioned adjacent an end of the sheath, as shown in FIG. 13. In FIG. 13, the space devoid of reinforcement layer structure, positioned adjacent an end of the sheath, can be at least partially occupied by a radiopaque element 228.

As with the outer jacket 140 shown in FIG. 10, the tapered outer jacket 240 is shown as having a first jacket portion 242 with a first material composition being positioned adjacent a proximal end 11 and a second jacket portion 244 with a second material composition being positioned adjacent a distal end 13. The first jacket portion 242 and the second jacket portion 244 are coaxially and tandemly disposed over structures of a reinforcement layer 230. The first jacket portion 242 and the second jacket portion 244 are respectively in contact with a radial outer surface of the inner liner 20. Nonetheless, the tapered outer jacket 240 can have a substantially homogeneous material composition from the first portion 242 to the second portion 244 while still providing the jacket with a nonuniform axial-stiffness.

Other Embodiments

The principles described herein are not limited to the descried embodiments. Using the principles disclosed herein, those of ordinary skill will appreciate a wide variety of possible embodiments of nonuniform axial-stiffness ureteral access sheath and associated methods.

For example, some disclosed methods can include providing an elongated tubular inner liner, the elongated tubular inner liner having a proximal end and a distal end; coaxially placing a tubular reinforcement layer over the inner liner; applying at least a first composition layer of first material over the reinforcement layer at the proximate end and a second composition at the distal end.

Innovative principles disclosed herein can be embodied in a variety of structures which provide nonuniform axial-stiffness over the length of the ureteral access sheath. Those skilled in the art will also recognize that combinations of the above referenced embodiments may be used in order to provide a structure with specific and desired combinations of axial-stiffness, torqueability, and pushability over the length of the ureteral access sheath.

For ureteral use, the overall length of the ureteral access sheath can be, for example, from 20 cm to 55 cm, with the outer diameter being less than 16 Fr (1 Fr=0.0135 inch). These dimensions are approximate, and in practical terms, depend upon sizes suitable for a particular purpose.

Innovative construction techniques disclosed herein can include coating, extruding, or otherwise forming the outer jacket so as to have a predetermined non-uniformity of axial-stiffness wherein a lower axial-stiffness at the distal end provides a softer, better tracking ureteral access sheath, and a higher axial-stiffness at the proximal end to provide improved pushability.

Innovative construction techniques disclosed herein can include coating, extruding, and otherwise forming the outer jacket so as to have a predetermined non-uniformity of axial-stiffness in cooperative arrangement with a reinforcement layer of a predetermined non-uniformity of longitudinal axial-stiffness encapsulated between the inner liner and outer jacket, wherein a lower axial-stiffness at the distal end provides a softer, better tracking device, and a higher axial-stiffness at the proximal end to provide improved pushability.

Therefore, we claim as my invention all that comes within the scope and spirit of the following claims.

What is claimed:

1. A non-uniform axial-stiffness ureteral access sheath, comprising:
   an inner liner;
   a reinforcement layer adjacent the inner liner; and
   an outer jacket adjacent the reinforcement layer and having an outer surface tapered along its length, the outer jacket comprising:
      a first proximal jacket portion having a first end and an opposing second end;
      a second distal jacket portion having a first end and an opposing second end;
   wherein the second jacket portion has a lower durometer than the first jacket portion, the first and second jacket portions have the same uniform thickness and the first end of the second jacket portion section abuts the second end of the first jacket portion.

2. The ureteral access sheath of claim 1, wherein the reinforcement layer is a coil having a tapered outer diameter and uniform inner diameter.

3. The ureteral access sheath of claim 2, wherein the coil is a metal.

4. The ureteral access sheath of claim 2, wherein the coil is both a metal and a polymer.

5. The ureteral access sheath of claim 2, wherein the coil has a diameter which varies from a proximal portion to a distal portion along the length of the longitudinal axis of the reinforcement layer.

6. The ureteral access sheath of claim 2, wherein the coil is a round or a flat coil.

7. The ureteral access sheath of claim 2, wherein the coil comprises angled or circumferential windings.

8. The ureteral access sheath of claim 2, wherein the coil has a pitch and a diameter that vary from a proximal portion to a distal portion along the length of the longitudinal axis of the ureteral access sheath.

9. The ureteral access sheath of claim 1, wherein the reinforcement layer comprises a tapered tubular mesh.

10. The ureteral access sheath of claim 1, wherein the reinforcement layer is at least partially occupied by a radiopaque element.

11. The ureteral access sheath of claim 1, wherein the reinforcement layer comprises a reinforcing composite material.

* * * * *